US00PP09909P

United States Patent [19]

Ackerman et al.

[11] Patent Number: Plant 9,909

[45] Date of Patent: Jun. 3, 1997

[54] STRAWBERRY PLANT NAMED 'PS-1031'

[75] Inventors: Stephen M. Ackerman, Salinas; Steven D. Nelson; Michael D. Nelson, both of Watsonville; Peter Salm, Capitola; Daniel T. Schmida, Watsonville, all of Calif.

[73] Assignees: Plant Sciences, Inc.; Berry Red, Inc., both of Watonsville, Calif.

[21] Appl. No.: 584,222

[22] Filed: Jan. 11, 1996

[51] Int. Cl.[6] ..... A01H 5/00

[52] U.S. Cl. ..... Plt./49

[58] Field of Search ..... Plt./48, 49

*Primary Examiner*—James R. Feyrer

*Attorney, Agent, or Firm*—Foley & Lardner

[57] ABSTRACT

This invention relates to a new and distinct winter planted short-day-type variety of strawberry known as 'PS-1031'. This new variety is primarily adapted to the growing conditions of the central coast of California. It is particularly characterized by its strong vigorous plant with high yields, short petiolule length, large berry size and its ability to remain in fruit production from early April through November in Salinas, Calif. The fruit is particularly identifiable by its seedy tipped primaries and longitudinal creases occurring primarily during the spring months. The fruit is very attractive during the summer and fall months with acceptable flavor, firmness and holding quality.

4 Drawing Sheets

SUMMARY OF THE INVENTION

The present invention relates to a new and distinct short-day-type strawberry variety designated as 'PS-1031'. This new variety is a result of a cross of the variety claimed in U.S. Plant Pat. No. 8,205, and now designated 'PS-118', and 'Muir' (U.S. Plant Pat. No. 6,558). The variety is botanically known as *Fragaria×ananassa* Duch.

This new variety of strawberry resulted from a breeding program jointly sponsored by Plant Sciences, Inc. and Berry R&D, Inc., both of Watsonville, Calif., with the objective of developing new and distinct strawberry varieties. The seedling resulting from the sforementioned cross was asexually propagated by stolons in a nursery located in Lassen County, Calif., and was subsequently selected from a controlled breeding plot in Watsonville, Calif. in 1991. After its selection, the new variety was further asexually propagated in Lassen County, Calif., by stolons and extensively tested over the next several years in fruiting fields near Watsonville, Calif. This propagation and reproduction has demonstrated that the combination of traits disclosed herein as characterizing the new variety are fixed and remain true to type through successive generations of asexual reproduction.

BRIEF DESCRIPTION OF THE FIGURES

The accompanying color photographs show typical specimens of the new variety at various stages of development as nearly true as it is possible to make in color reproductions.

DESCRIPTION OF THE NEW VARIETY

Figure 1:
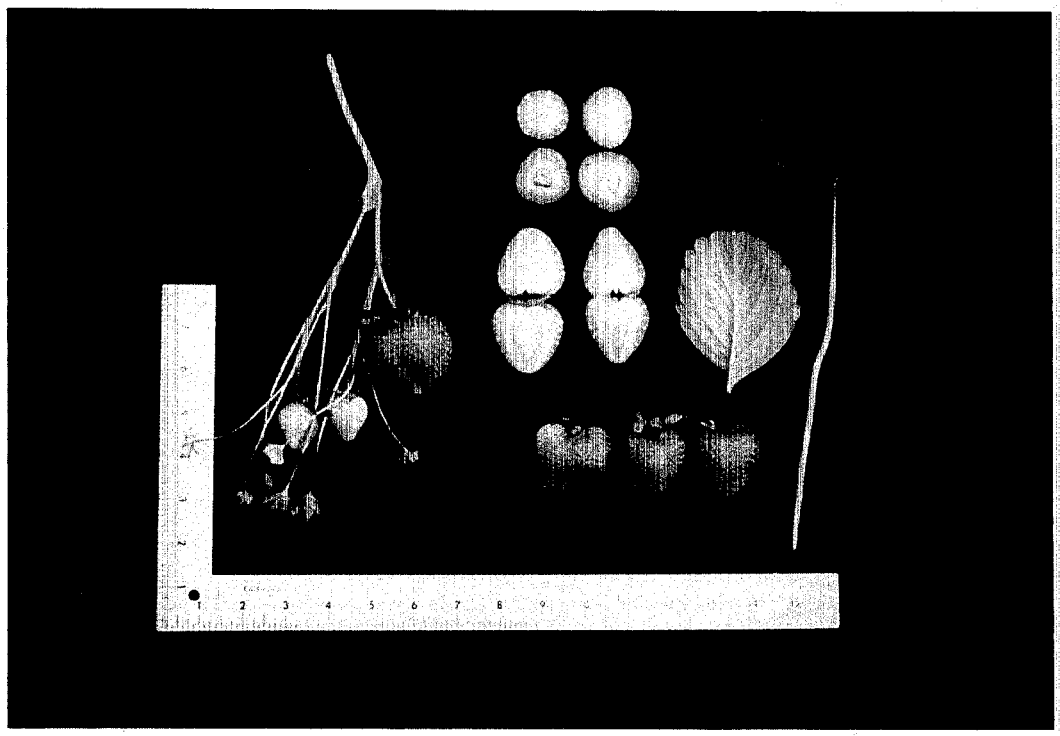
FIG. 1 shows typical plant parts of the new variety including leaves (both the lower surface of a mature terminal leaflet, and the upper surface of a mature trifoliate leaf). Cross-sectional and longitudinal views of mature fruit illustrate typical light flesh, and, conspicuous core and core cavity. Also shown is an inflorescence with the primary berry being mature and harvestable demonstrating typical fruit distribution, shape and size.
Figure 2:
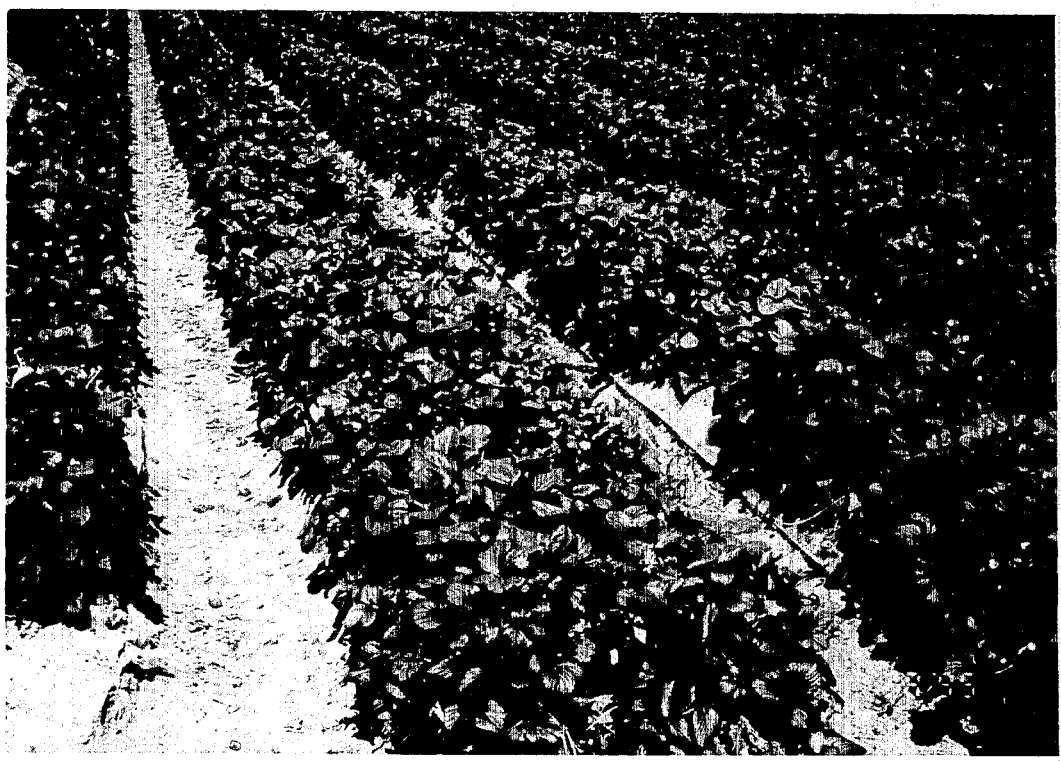
FIG. 2 shows typical plant growth, flowering and fruiting characteristics in late July 1995. The photograph illustrates the plant vigor, inflorescences, and upright growth habit.
Figure 3:
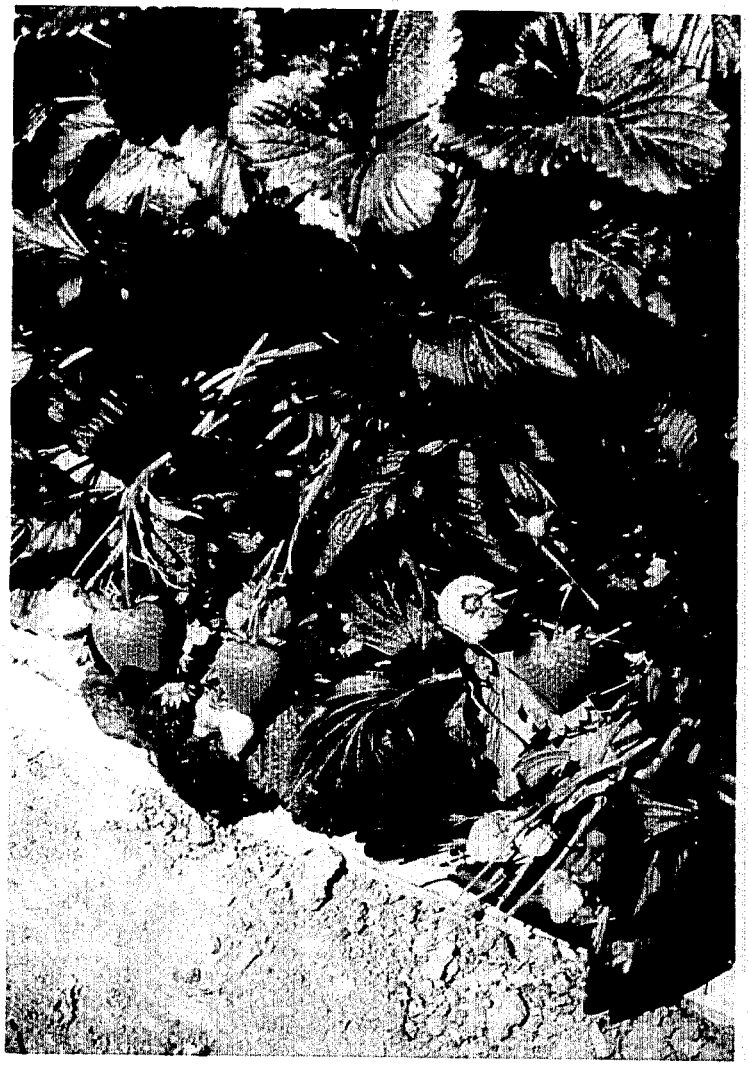
FIG. 3 shows a close-up of typical plant growth, flowering and fruiting characteristics in late July 1995.
Figure 4:
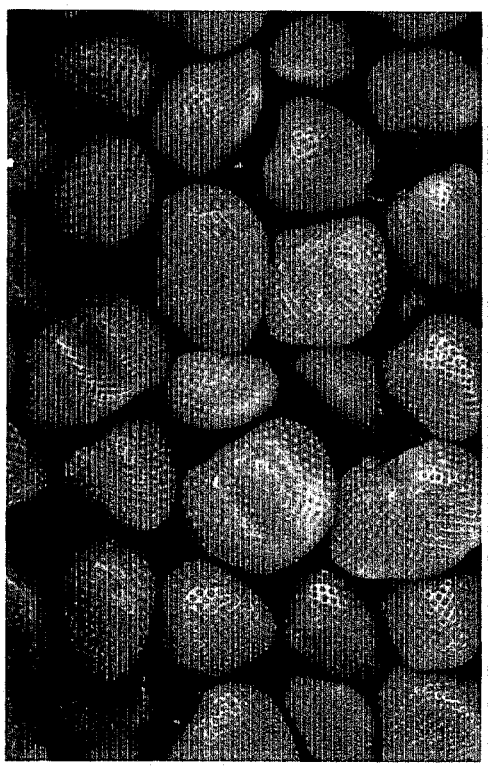
FIG. 4 shows a close-up view of fruit harvested in mid July 1995 and packed in a standard twelve-dry-pint-crate.
Figure 4:
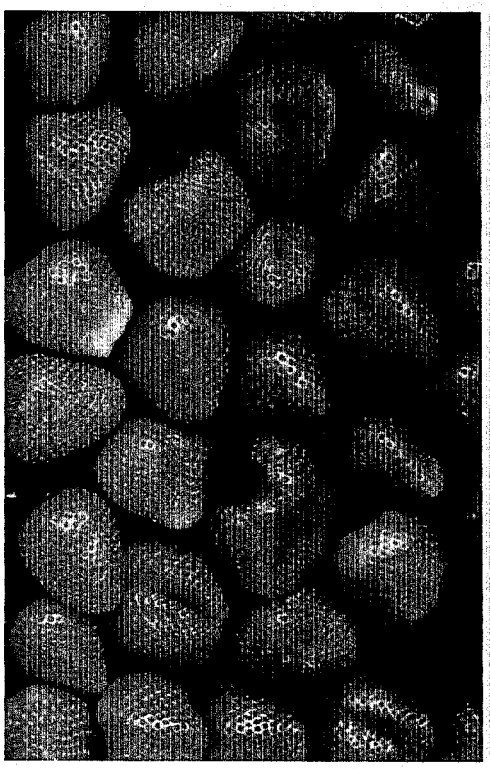

'PS-1031' is primarily adapted to the climate and growing conditions of the central coast of California. This region provides the necessary winter temperatures required for it to produce a strong vigorous plant that remains in fruit production from April through November. The nearby Pacific ocean provides the needed humidity and cool temperatures to maintain fruit quality during the summer production months.

'PS-1031' is a large vigorous plant. When provided with optimum chilling in the nursery propagation fields prior to being dug, and artificial cold storage prior to being planted, the plant of the new variety is larger and more vigorous than the varieties 'PS-118' or 'Selva' (U.S. Plant Pat. No. 5,266). 'PS-1031' generally produces more runners per plant in the fruiting fields than either 'PS-118' or 'Selva'. The foliage of the new variety is noticeably lighter in color than 'PS-118' but is similar in color to 'Selva'. 'PS-1031' leaves are larger and less rounded than 'PS-118', but are similar in size and shape to 'Selva'. 'PS-1031' has more serrations per leaf than 'PS-118' and fewer serrations than 'Selva'. These serrations are also deeper than both. Petioles are longer in length than either 'PS-118' or 'Selva' and larger in diameter than 'PS-118'. Petiolule length of 'PS-1031' is considerably shorter than both 'PS-118' and 'Selva'. Table 5 provides foliage characteristics of 'PS-1031', 'PS-118' and 'Selva'.

'PS-1031' is capable of long season fruit production with fruit of excellent size and good quality during teh entire season when provided with optimum chilling in the nursery propagation fields and artificial cold storage prior to being planted. Initial studies indicate that 'PS-1031' has a lower vernalization (chilling) requirement than 'Selva' in order to optimize fruit production and plant vigor. Fruit production begins as early as the beginning of April in Salinas, Calif., and may continue into November if rains and cold temperatures do not prevent the harvest. April production is earlier and heavier than 'PS-118' and similar to 'Selva'. 'PS-1031' season average fruit size is larger than either 'PS-118' or 'Selva', with total yields greater than both (Table 1).

The fruit of 'PS-1031' is smoother with fewer longitudinal creases and better overall appearance and gloss than 'Selva'. Table 3 provides a summary of fruit quality performance ratings. The primary berries of 'PS-1031' tend to produce seedy tips at the apex of the fruit primarily during the early spring and under adverse weather conditions. In comparison, 'PS-118' tends to produce seedy tipped fruit during much of the season. The seeds of 'PS-1031' are typically held even with the surface of the fruit. In contrast, the seeds of 'PS-118' tend to protrude from the surface of the fruit. The fruit color of 'PS-1031' is noticeably lighter than 'PS-118' but similar in color to 'Selva'. 'PS-1031' has a lighter internal flesh color than either 'PS-118' dor 'Selva'. The early spring fruit of 'PS-1031' is less uniformly shaped than 'PS-118' with more longitudinal creases and wedge-shaped berries. By mid-summer the fruit of 'PS-1031' becomes more uniformly conic in shape than either 'PS-118' and 'Selva'.

Flavor panels have rated 'PS-1031' as having nearly comparable flavor to 'Selva' (Table 4). The fruit of 'PS-1031' is more susceptible to skin cracking from rain than either 'PS-118' or 'Selva'. The total inflorescence length of 'PS-1031' is longer than 'PS-118' and shorter than 'Selva', especially during the summer months. The average primary peduncle length of 'PS-1031' is similar in length but thinner than 'PS-118' or 'Selva'. The primary pedicel of 'PS-1031' is shorter than 'Selva' and generally thinner than 'Selva' or 'PS-118'. Flowers and ripening fruit are less visible above the canopy of the plant than 'PS-118'. A summary of inflorescence characteristics for 'PS-1031', 'PS-118' and 'Selva' is contained in Table 6.

SPECIFIC DESCRIPTION OF THE NEW VARIETY

The following is a detailed description of 'PS-1031', including the variety's morphological, electrophoretic, pest and disease reaction characteristics. This detailed description is based on observations taken during May through July of 1995 in Salinas, Calif. Inthose instances in which characteristics were rated at different times, the date of evaluation is listed. These measurements and ratings were made from plants dug from a high-elevation nursery located in Lassen County, Calif. in October 1994 and planted in Salinas, Calif. in November 1995. The phenotypic characteristics of the new variety may vary slightly, depending upon variations in environmental factors, including weather (temperature, humidity and light intensity), day length, soil type, location, and time of year, without any change in the genotype of the plant. 'PS-1031' has not been observed under all possible environmental conditions. Color terminology follows the Munsell Book of Colors, Munsell Color, Baltimore, Md. (1976).

FRUIT CHARACTERISTICS

'PS-1031' fruit, fruit production and runner production (fruiting field) characteristics are compared to those of 'PS-118' and 'Selva' in Table 1.

TABLE 1

1994 market fruit yield, fruit size and runner production characteristics from plants harvested from April through November 1994 of 'PS-1031' from a high elevation nursery (McArthur, California) compared with standard cultivars dug October 20, 1993 and planted November 9, 1993 in Salinas, California.

| CULTIVAR | APRIL YIELD GM/PL | TOTAL YIELD GM/PL | AVERAGE FRUIT SIZE G/FR | AVERAGE RUNNERS/ PL |
|---|---|---|---|---|
| 'PS-1031' | 81 | 1625 | 24.8 | 0.50 |
| 'PS-118' | 43 | 1351 | 21.7 | 0.12 |
| 'SELVA' | 90 | 1414 | 22.8 | 0.20 |

TABLE 2

Comparison of primary fruit characteristics of 'PS-1031', 'PS-118' and 'Selva' from Salinas, California, July 27, 1995*.

| CHARACTER | 'PS-1031' | 'PS-118' | 'SELVA' |
|---|---|---|---|
| Munsell Color | 7.5R 3/10 to 7.5R 4/10 | 7.5R 3/10 to 7.5R 2/8** | 7R 4/11** |
| Fruit Length mean (cm) | 3.7 | 3.8 | 4.4 |
| Fruit Width mean (cm)*** | 4.1 | 4.0 | 4.2 |
| Calyx Diameter mean (cm) | 4.3 | 5.4 | 4.1 |
| Sepals/Berry mean | 14.8 | 15.0 | 15.8 |

*'PS-118' and 'Selva' evaluated July 17, 1995.
**'PS-118' and 'Selva' fruit color according to Nelson et al. U.S. Plant Pat. No. 8,205.
***Width is measured across the widest part of the berry, typically the shoulders.

TABLE 3

Comparison of 1994 fruit quality characteristics of 'PS-1031', 'PS-118' and 'Selva' from Salinas, California.*

| CHARACTER | 'PS-1031' | 'PS-118' | 'SELVA' |
|---|---|---|---|
| Skin Firmness | 7.3 | 8.3 | 7.6 |
| Fruit Appearance | 7.0 | 7.7 | 6.8 |
| Fruit Gloss | 7.5 | 8.2 | 6.6 |

*Results are from replicated holding tests performed from April through October 1994. Ratings are based on a scale from 1–10; the higher the rating, the stronger the skin and the more attractive and glossy the berry.

TABLE 4

Comparison of 1995 flavor test summary of 'PS-1031', 'PS-118' and 'Selva'.*

| CHARACTER | 'PS-1031' | 'PS-118' | 'SELVA' |
|---|---|---|---|
| Rating | 2.0 | 3.5 | 2.4 |

*Results are an average of 3–4 flavor tests from fruit harvested from Salinas, California after being held for 2–3 days in cold storage. Ratings are based on scores of 1–5, 5 being the best.

The fruit of 'PS-1031' is large in size and characteristically symmetrically conic in shape from about mid-June through November. Primary berries are typically wider to equal across the shoulders than long with longitudinal creases and irregular shapes commonly occurring. The secondary and tertiary berries are typically longer than wide and mostly symmetrically conic in shape. The fruit surface is medium red in color with a very light colored flesh to white at the core. See Table 2 for fruit comparison characteristics.

The fruit surface is typically smooth with the seeds generally held flush to the surface with some seeds slightly protruding from the surface of the fruit. The seeds are yellow and only darken slightly with prolonged exposure to direct sunlight. The seeds are generally spaced evenly over the surface of the berry with seedy tipped fruit commonly occurring during the early spring. These berries may develop severe creases radiating longitudinally from the seedy tips to the shoulders of the fruit. The fruit becomes more uniformly shaped with fewer seedy tips and longitudinal creases during the summer and fall months. The skin of the fruit is considered moderately firm with acceptable gloss. Tables 3 and 4 summarize fruit quality and flavor characteristics, respectively.

The calyx of the primary berry is medium in diameter with some overlapping sepals. The calyx attaches slightly below the base of the fruit with necked fruit very uncommon. The sepals are elliptical to ovate in shape with acute apexes and only occasionally serrated. Fruit skin is considered very susceptible to cracking due to rain. Pollination may be affected by rain resulting in seedy tipped fruit and small malformed berries.

PLANT CHARACTERISTICS

The plant of 'PS-1031' is large in size with multiple crowns producing few runners if given the proper chilling levels prior to being dug, and artifically, prior to being planted. Excessive chilling will result in an over-vigorous plant with a reduction in total fruit yield and increased runner production. The foliage grows upright on relatively long thick petioles. The plant canopy remains relatively open if exposed to the proper chilling and cold storage levels, but may become dense if over-chiled and/or overstored. The plant canopy has a relatively medium-light colored appearance.

FOLIAGE CHARACTERISTICS

'PS-1031' foliage characteristics are compared to those of 'PS-118' and 'Selva' in Table 5.

TABLE 5

Comparison of leaf characteristics of 'PS-1031', 'PS-118' and 'Selva' from Salinas, California, May 19, 1995.

| CHARACTER | 'PS-1031' | 'PS-181' | 'SELVA' |
|---|---|---|---|
| Munsell Leaf Color (upper Surface) | 7.5GY 3/4 to 7.5GY 2/4 | 7.5GY 3/4* | 7.5GY 4/4* |
| Terminal Leaflet Length mean (cm) | 9.9 | 8.4 | 9.8 |
| Terminal Leaflet Width mean (cm) | 8.2 | 7.7 | 8.3 |
| Terminal Leaflet ratio (L/W) | 1.21 | 1.09 | 1.19 |
| Petiole Length mean (cm) | 22.9 | 20.1 | 19.8 |
| Petiole Width mean (mm) | 5.3 | 4.7 | 5.2 |
| Petiolule Length mean (mm) | 5.9 | 10.0 | 10.8 |

TABLE 5-continued

Comparison of leaf characteristics of 'PS-1031', 'PS-118' and 'Selva' from Salinas, California, May 19, 1995.

| CHARACTER | 'PS-1031' | 'PS-181' | 'SELVA' |
|---|---|---|---|
| Serrations/leaf | 22.1 | 20.7 | 24.9 |
| Serration depth mean (mm) | 6.4 | 5.8 | 5.2 |

*'PS-118' and 'Selva' leaf color according to Nelson et al., U.S. Plant Pat. No. 8,205.

The foliage of 'PS-1031' is relatively large in size, moderately glossy, medium-light in color and moderately rugose. The terminal leaflet is much longer than wide as described by the length/width ratio. Table 5 summarizes foliage comparison characteristics. Leaflets have many relatively large and deep serrations at the margins, with moderately acute apexes. These serrations typically occur singly, very seldom in doubles. Petioles are considered long and thick in diameter with bract leaflets commonly occurring singly or in pairs. Petiolules are considered short in length. Pubescence on the petioles grow irregularly perpendicular to the petiole and irregularly parallel to the upper and lower leaf surface.

FLOWERS AND INFLORESCENCES

'PS-1031' inflorescence characteristics are compared to those of 'PS-118' and 'Selva' in Table 6.

TABLE 6

Comparison of inflorescence charateristics of 'PS-1031', 'PS-118' and 'Selva' from Salinas California, July 27, 1995*.

| CHARACTER | 'PS-1031' | 'PS-118' | 'SELVA' |
|---|---|---|---|
| Inflorescence Length mean (cm) | 32.9 | 30.8 | 36.0 |
| Primary Peduncle Length mean (cm) | 19.2 | 19.0 | 20.0 |
| Primary Peduncle Width mean (mm) | 3.6 | 4.2 | 4.2 |
| Primary Pedicel Length mean (cm) | 6.8 | 6.3 | 9.0 |
| Primary Pedicel Width mean (mm) | 2.2 | 2.3 | 2.5 |

*'PS-118' and 'Selva' evaluated July 17, 1995.

The inflorescences of 'PS-1031' are medium in length, extending the flowers and fruit beyond the foliage during the spring months. As the plant grows and becomes more vigorous during the summer and fall, the fruit may remain slightly concealed within the canopy of the plant. The primary peduncle is considered medium in length and thickness, especially at the time of the evaluation. The pedicel holding the primary berry is considered medium-short in length and thin and may originate singly from the apex of the primary peduncle or from one of the secondary peduncles. Secondary and tertiary berries are borne on pedicels arising from secondary peduncle apexes. Table 6 summarizes inflorescence comparison characteristics.

Flowers are large in size and seldom visible above the canopy of the plant. Anthers produce ample pollen for good pollination except during the early season and rainy periods when seedy tips and creased fruit may occur. Flowers produce an average of 5 to 8 obovate shaped petals per flower. Typically a single bract leaf is borne on a short petiole which originates at the primary peduncle apex alongside the base of one of the secondary peduncles. Occasionally a trifoliate will develop instead of the single bract leaf. Bract leaves may also occur singly at the apex of secondary peduncles. Pubescence occurs on all peduncles and pedicels, growing irregularly perpendicular to both these surfaces.

ISOZYMES IN LEAF EXTRACT

'PS-1031' isozyme banding characteristics are compared to those of 'PS-118' and 'Selva' in Table 7.

TABLE 7

'PS-1031' Isozyme banding patterns compared to 'PS-118' and 'Selva'.

| CULTIVAR | PGI | PGM |
|---|---|---|
| 'PS-1031' | A4 | C2 |
| 'PS-118' | A7 | C4 |
| 'Selva' | A2 | C2 |

Studies of protein polymorphism in strawberry by the starch gel electrophoresis method were conducted at Plant Sciences, Inc. to characterize this newly developed variety and distinguish it from similar appearing varieties.

Isozymes were extracted from young leaves and characterized, using starch gel electrophoresis techniques. The following isozymes were characterized: phosphoglucoisomerase (PGI: EC 5.3.1.9) and phosphoglucomutase (PGM: EC 2.7.5.1).

The testing used both field and greenhouse grown plant material, all grown in Watsonville, Calif. Newly mature leaves (0.5 g fresh weight) from the growing crowns were used. Samples were collected in the morning, held at 4° and analyzed within six hours.

The tissue preparation, extraction and staining methods utilized are as reported in S. Arulsekar and D. E. Parfitt, "Isozyme Analysis Procedures for Stone Fruits, Almong, Grape, Walnut, Pistachio, and Fig", HortScience 21(4): 928–933.

Following electrophoresis, the gel was sliced and stained for each enzyme system. Banding patterns were interpreted as they developed, and gel slices were fixed in 50% glycerol.

Figure 5:
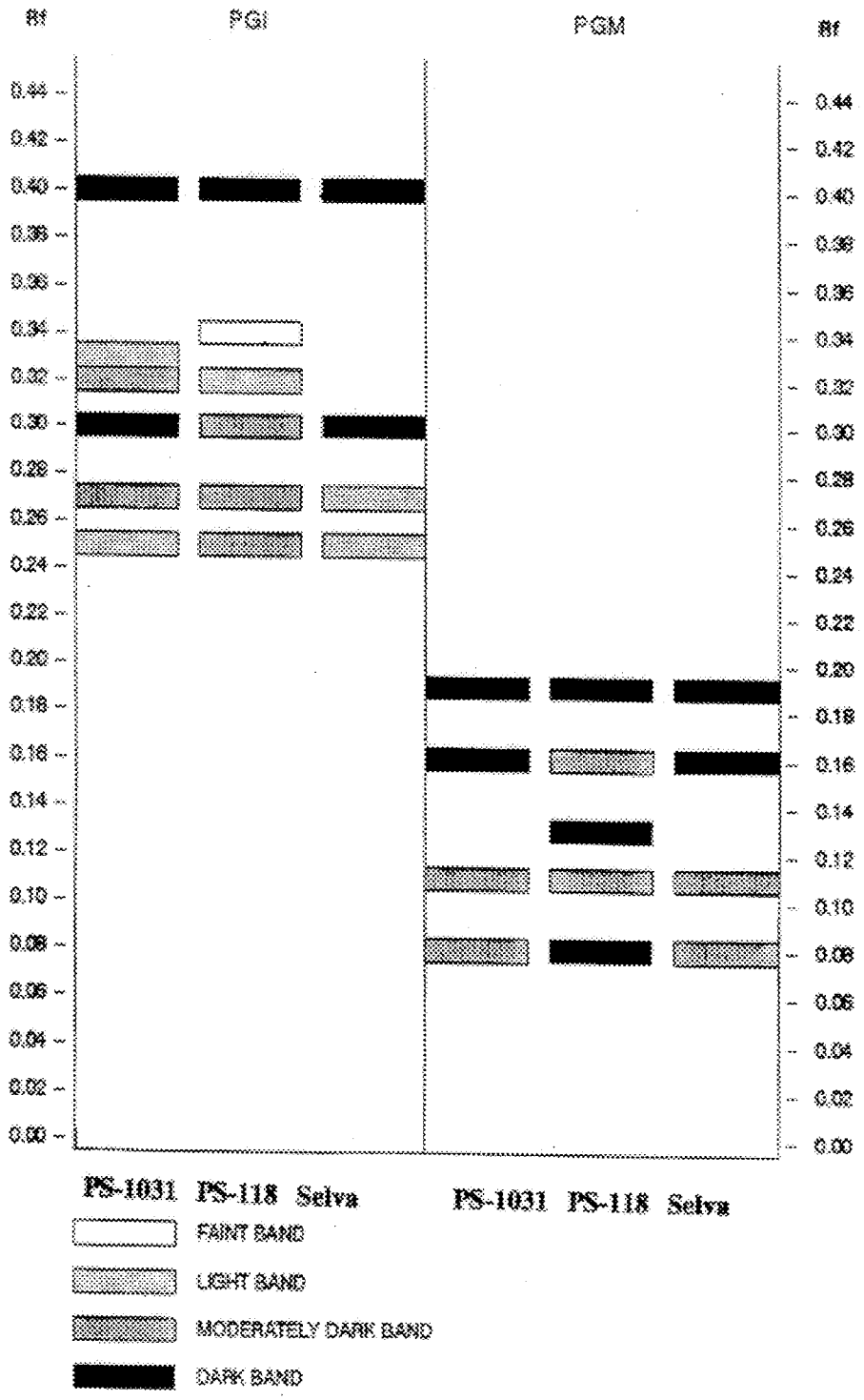
FIG. 5 disclosed the isozyme banding patterns for 'PS-1031' compared with those of 'PS-118' and 'Selva'.

The isozyme banding patterns of 'PS-1031', compared to 'Selva' and 'PS-118', are given in FIG. 5. The pattern and band densities for PGM are distinctly different between 'PS-1031' (C2) and 'PS-118' (C4). The pattern and band densities for PGI are distinctly different between 'PS-1031' (A4) and both 'PS-118' (A7) and 'Selva' (A2). The combination of isozyme patterns shown, derived from specific techniques described, and the other characteristics of 'PS-1031' identify it with certainty as a unique strawberry variety.

A series of molecular markers have been assigned to this new variety for unique identification.

PEST REACTIONS

The new variety may not be resistant to any of the known insects, diseases or viruses common in California. It is known to be susceptible to the two-spotted spider mite, aphid and flower thrip. It is also known to be susceptible to grey fruit mold, angular leafspot and powdery mildew. The susceptibility of the new variety to any of the virus complexes of California has not been determined.

We claim:

1. A new and distinct variety of strawberry plant designated 'PS-1031', as herein described and illustrated.

* * * * *

ISOZYME BANDING PATTERNS